United States Patent [19]

Wark

[11] Patent Number: 5,754,524

[45] Date of Patent: May 19, 1998

[54] COMPUTERIZED METHOD AND SYSTEM FOR ANALYSIS OF AN ELECTROPHORESIS GEL TEST

[76] Inventor: Barry J. Wark, 1588 Northrop, Falcon Heights, Minn. 55108

[21] Appl. No.: 705,781

[22] Filed: Aug. 30, 1996

[51] Int. Cl.⁶ ............................................. G01N 27/26
[52] U.S. Cl. ............................................. 364/497; 204/461
[58] Field of Search .................................. 364/496, 497, 364/498, 499, 550; 204/456, 461, 462; 250/580, 583; 356/344

[56] References Cited

U.S. PATENT DOCUMENTS

| | | | |
|---|---|---|---|
| 4,329,591 | 5/1982 | Fujiwara et al. | 250/548 |
| 4,638,456 | 1/1987 | Elias et al. | 364/518 |
| 4,707,235 | 11/1987 | Englert et al. | 204/182.8 |
| 4,720,786 | 1/1988 | Hara | 204/461 |
| 4,837,687 | 6/1989 | Tanaka et al. | 250/580 |
| 4,865,968 | 9/1989 | Orgel et al. | 204/462 |
| 4,987,066 | 1/1991 | Epplen | 435/6 |
| 5,061,067 | 10/1991 | Yamamoto et al. | 356/344 |
| 5,073,963 | 12/1991 | Sammons et al. | 382/30 |
| 5,171,534 | 12/1992 | Smith et al. | 422/82.05 |
| 5,277,780 | 1/1994 | Kambara | 204/299 R |
| 5,311,600 | 5/1994 | Aghajan et al. | 382/14 |
| 5,351,305 | 9/1994 | Wood et al. | 382/6 |
| 5,400,249 | 3/1995 | Soll et al. | 364/498 X |
| 5,436,129 | 7/1995 | Stapleton | 435/6 |
| 5,451,500 | 9/1995 | Stapleton | 435/6 |
| 5,464,945 | 11/1995 | Reynolds et al. | 536/24.31 |

*Primary Examiner*—James P. Trammell
*Assistant Examiner*—M. Kemper
*Attorney, Agent, or Firm*—Schwegman, Lundberg, Woessner & Kluth, P.A.

[57] ABSTRACT

A computerized method for analyzing results of an electrophoresis gel test having a plurality of lanes is disclosed. The results include a reference lane and at least one sample lane. Each lane has one or more bands located throughout the lane. The method comprises four steps. The first step digitizes the results of the electrophoresis gel test into a corresponding compute-readable format. The second step detects the location of each band within each lane based on the computer-readable format of the results. The third step determines a characteristic based on the location of each band and the length of a segment corresponding to the band. The fourth step compares the location of each band within each sample line with the characteristic as applied to a predetermined profile to determine if any sample lane matches the profile.

21 Claims, 3 Drawing Sheets

COMPUTERIZED METHOD AND SYSTEM FOR ANALYSIS OF AN ELECTROPHORESIS GEL TEST

FIELD OF THE INVENTION

This invention relates generally to electrophoresis gel testing, and more particularly to computerized analysis of the results of such testing.

BACKGROUND OF THE INVENTION

As understood within the medical community, a genetic disorder results in the mutation of a particular gene. Comparison of a sample gene against the profile for a particular disorder, therefore, is useful in determining whether the patient from which the sample was taken is afflicted with the disorder. A profile for a genetic disorder is simply the set of DNA segments, the presence of each of which within a sample gene indicating that the gene is afflicted with the disorder.

Genetic sampling for this type of genetic testing warrants obtaining a DNA sample from a particular polymorphic region of a human genome. The human genome contains approximately $10^7$ to $3 \times 10^7$ polymorphic regions. A particular polymorphic region of DNA either in the gene or linked to the gene changes length or sequence upon the mutation that results from being afflicted with a genetic disorder. Thus, isolation and identification of a particular polymorphic region must precede its testing for the genetic disorder.

To properly isolate and identify a polymorphic region of DNA, a restriction analysis is performed. This involves the use of a restriction enzyme, which literally "cuts" the DNA sample of a patient, so that only the desired polymorphic region is analyzed. If a gene is afflicted with a particular genetic disorder, then the restriction enzyme will cut the gene into a DNA sample having at least the DNA segments in the profile for that disorder. Quantification and measurement of these sample DNA segments is, therefore, the focal point in comparing a sample gene against the profile for a genetic disorder.

Electrophoresis gel testing is a method commonly used to effectuate this quantification and measurement. Electrophoresis involves the separation of DNA segments within both a genetic sample and an arbitrary but known reference set of DNA segments according to their relative mobilities through a polymer network, or gel, under the influence of an electric potential. The electrophoresis of the genetic sample can then be compared to the profile for the genetic disorder to determine if the sample is afflicted with the disorder.

To prepare a genetic sample that has been separated by a restriction enzyme for electrophoresis, it is first subjected to a polymerase chain reaction. This chain reaction amplifies the quantity of each segment within the separated sample, so that a proper electrophoresis can be accomplished. The sample is then loaded into one or more lanes of an electrophoretic gel, and an arbitrary but known reference set of DNA segments is loaded into another lane of the gel. The arbitrary but known reference set includes DNA segments of known lengths.

To conduct electrophoresis on the gel, an electric potential is applied to the gel for a certain period of time. In this manner, charged segments of the samples and the reference set move in parallel directions for various distances depending on their relative mobilities.

The DNA segments migrate in the direction of the current on a logarithmic basis dependent on their length, with smaller fragments moving faster and therefore farther. The test results in each lane have one or more bands located throughout the lane, each corresponding to a DNA segment.

To analyze the test results, the bands of the sample lane are examined to determine whether the sample matches the profile for the genetic disorder. If a sample matches the profile, in that for every segment in the profile there is a band in the sample lane representing a corresponding segment in the sample, then the test is considered positive. That is, the patient from which the DNA sample was taken carries a polymorphism in a genome that corresponds to a known mutation of the gene of the particular disorder being tested for.

Typically, analysis of the electrophoresis test results is accomplished visually by a trained doctor or technician. The trained professional examines the test results and decides if for every segment in the profile there is a band present in the sample lane representing a corresponding segment. The trained professional does this by examining the location of each band within the sample lane against the bands within the reference lane, the latter bands representing segments of known length. The bands within the reference lane allow the professional to estimate the length of a segment represented by a given band by gauging the location of that band against the location of the bands within the reference lane that represent segments of known lengths. If a sample lane includes properly located bands of sufficient density, then there is a match between the sample lane and the profile.

However, this technique has several shortcomings. Foremost, great subjectivity is introduced into the analysis. Individual labs, and even individual doctors and technicians, may have different testing and training procedures, such that there is no objective standard that can be guaranteed among different labs or trained personnel. This impairs the credibility that can be associated with any particular analysis by any one individual. Thus, the reliability of the analysis is only as good as the person examining the test results.

Visual analysis is also quite difficult to conduct. The trained professional must determine whether a band is present in the proper place within the sample lane, such that the band corresponds to a segment of the profile of the genetic disorder being tested for, by comparison against the bands representing segments of known length within the reference lane. However, because the bands are separated from one another on a logarithmic scale, this comparison is very unintuitive. That is, great experience in analysis is required so that the professional does not improperly examine the bands of the sample lane against the bands of the reference lane in a linear manner.

Furthermore, human analysis of the electrophoresis test results may increase the cost of running the test by requiring the attention of a highly skilled doctor or technician. The time needed to analyze test results may also detract the doctor or technician from other duties. Finally, in areas where electrophoresis testing equipment is present but personnel sufficiently skilled in analysis thereof are not, there may be an undesirable delay in getting the results properly analyzed because they have to be shipped to a different location.

Therefore, there is a need for analysis of electrophoresis testing that provides for reliable and objective analyses that are not of suspect credibility. There is also a need for such analysis to be performed at minimal added cost to the electrophoresis testing process.

Finally, there is a need for such analysis without the necessity of significant attention from a trained doctor or technician.

SUMMARY OF THE INVENTION

This invention relates to a computerized method and system for analyzing results of an electrophoresis gel test. The results of the electrophoresis gel test has a plurality of lanes, including a reference lane and at least one sample lane. Each lane has one or more bands located throughout the lane.

In one embodiment of the invention, a method comprises four steps. The first step digitizes the results of the electrophoresis gel test into a corresponding computer-readable format. The second step detects the location of each band within each lane based on the computer-readable format of the results. The third step determines a characteristic based on the location of each band within the reference lane and the length of a corresponding segment. The fourth step compares the location of each band within each sample lane with the characteristic as applied to a predetermined profile to determine if any sample lane matches the profile.

In this manner, the present invention provides a number of advantages. The analysis of the results of the electrophoresis gel test is accomplished via computer. Therefore, the analysis of the invention is objective and reliable; there is no chance that an improper analysis can be made as a result of a person being unaccustomed to the logarithmic nature of the results. Furthermore, because the analysis is automated, it does not require significant attention from a trained doctor or technician to be run.

In a second embodiment of the invention, a computerized system comprises a digitizer and a computer. The digitizer digitizes the results of the electrophoresis gel test into a corresponding computer-readable format. The computer comprises three means. A first means is for detecting the location of each band within each lane of the computer-readable format of the results. A second means is for determining a characteristic based on the location of each band within the reference lane and a corresponding segment. A third means is for comparing the location of each band within each sample lane with the characteristic as applied to a predetermined profile to determine if any sample lane matches the profile.

In a particular embodiment of the invention, the computer employed to automate the analysis according to the present invention is a typical desktop PC-compatible or Macintosh computer. In this manner, the present invention provides the advantage of added minimal cost to the electrophoresis testing process; off-the-shelf computer equipment, as opposed to highly expensive custom equipment, can typically be used. Such desktop computers are typically of lower cost than the remainder of the electrophoresis testing equipment by several orders of magnitude. Thus, the present invention effectuates low-cost analysis of the results of electrophoresis gel testing.

Other embodiments of the present invention include a computer-readable storage medium having a computer program executable on a suitably configured computer. The computer program directs the computer to perform the steps of the method as have been described. Still other and further embodiments, advantages and aspects of the present invention will become apparent in the following description and by reference to the accompanying drawings.

DETAILED DESCRIPTION OF THE DRAWINGS

Figure 1:
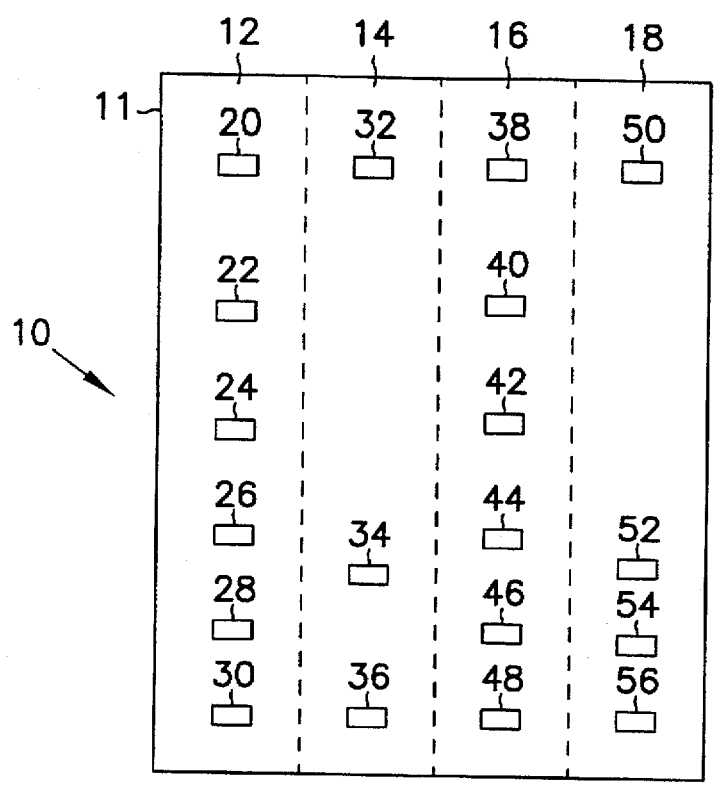
FIG. 1 is a diagram of typical results of an electrophoresis gel test.

The present invention effectuates computerized analysis of the results of electrophoresis gel testing. As shown in FIG. 1, typical results of an electrophoresis gel test are shown. Electrophoresis gel test results 10 has lanes 12, 14, 16 and 18. Each lane corresponds to a particular DNA sample. In one embodiment of the invention, one of lanes 12, 14, 16 and 18 corresponds to an arbitrary but known reference set of DNA segments, while the remaining lanes correspond to samples taken from a patient. For purposes of this description only, and not as a limitation of the invention, lane 12 is the reference lane, while lanes 14, 16 and 18 are the sample lanes. That is, lane 12 corresponds to an arbitrary but known reference set of DNA segments, while lanes 14, 16 and 18 correspond to the samples taken from a patient. The present invention is not limited to any particular manner in which test results 10 are obtained. Electrophoresis test apparatuses that produce results such as test result 10 of FIG. 1 are well known to those of ordinary skill in the art.

Each of lanes 12, 14, 16 and 18 comprise one or more bands. Lane 12 comprises bands 20, 22, 24, 26, 28 and 30; lane 14 comprises bands 32, 34 and 36; lane 16 comprises bands 38, 40, 42, 44, 46 and 48; and, lane 18 comprises 50, 52, 54 and 56. Each band corresponds to a DNA segment, that is, a series of DNA base pairs, that has migrated from the top of a lane downward, in response to exposure to the applied electric potential of the electrophoresis test. The shorter a segment is, the farther it travels downward in the lane. Note that, however, the actual lengths of the bands are substantially identical to one another, even though the lengths of their corresponding DNA segments are not. Note as well that each band starts from the same position at the beginning of the electrophoresis gel, which is herein referred to as the base line for the gel. This is shown in FIG. 1 as base line 11.

Thus, with respect to lane 12, the segment corresponding to band 30 is shorter and has traveled farther than has the segment corresponding to band 28; the segment corresponding to band 28 is shorter and has traveled farther than has the segment corresponding to band 26; the segment corresponding to band 26 is shorter and has traveled farther than has the segment corresponding to band 24; the segment corresponding to band 24 is shorter and has traveled farther than has the segment corresponding band 22; and, the segment corresponding to band 22 is shorter and has traveled farther than has the segment corresponding to band 20.

Similarly, with respect to lane 14, the segment corresponding to band 36 is shorter and has traveled farther than the segment corresponding to band 34, and the segment corresponding to band 34 is shorter and has traveled farther than the segment corresponding to band 32. With respect to lane 16, an ordering of the segments by length from smallest to longest, and an ordering of the segments by how far they have migrated from farthest to closest is, by their corresponding bands: band 48, band 46, band 44, band 42, band 40 and band 38. With respect to lane 18, a corresponding ordering of the bands by length from smallest to longest, and an ordering of the bands by how far they have migrated from farthest to least is, by their corresponding bands: band 56, band 54, band 52 and band 50. As to any one electrophoresis gel testing results, such as results 10 of FIG. 1, the distance that fragments of different lanes, but of equal length, migrate is identical. Furthermore, the distance that a fragment of one lane migrates is always less than that of a shorter fragment of another lane.

Figure 2:
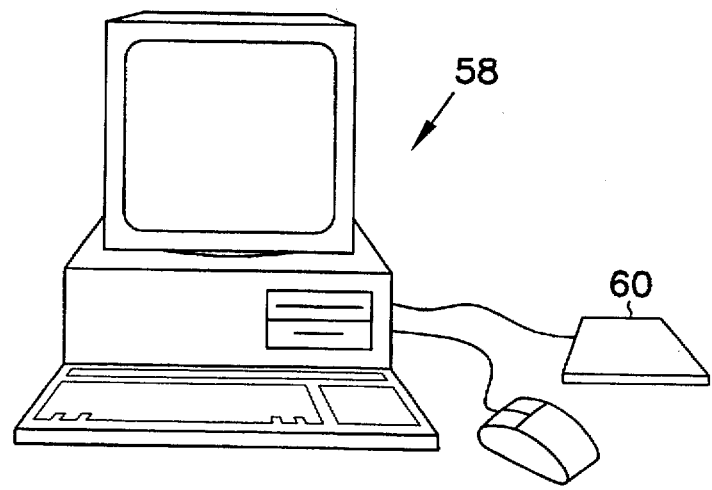
FIG. 2 is a diagram of one embodiment of the present invention.

Referring now to FIG. 2, a diagram of one embodiment of the present invention is shown. Computer 58 is operatively coupled to digitizer 60. Computer 58 has a program running thereon in accordance with the present invention, and typically includes a central processing unit (CPU), a storage device, and a random-access memory (RAM). The program in one embodiment resides on the storage device, and is copied into the RAM and executed therefrom by the CPU. The storage device is typically a hard disk drive, a floppy disk drive, or a tape cartridge drive, although the invention is not so limited. In the case where the storage device is a floppy disk drive, the program is stored on a floppy disk for insertion into the floppy disk drive. The present invention is not limited as to the type of computer 58. In one embodiment of the invention, computer 58 is an Apple Macintosh, however. In another embodiment, computer 58 is a PC-compatible computer. Furthermore, the present invention is not limited as to the programming language by which the computer program is implemented. However, in one embodiment of the invention, the programming language is C.

Digitizer 60 allows for the results of the electrophoresis test, such as test results 10 of FIG. 1, to be translated into a computer-readable format, i.e., a digitized image. Typically, electrophoresis test results exist as an image on paper or other printable material produced by a medical imaging device, or as an image resulting from developed photographic film. The present invention is not limited as to any particular type of digitizer. In one embodiment of the invention, digitizer 60 is an Apple QuickTake 150 digital camera. However, the digitizer could also be a flat-bed scanner, a sheet-fed scanner, or any other type of digitizer, without departing from the spirit and scope of the present invention. Furthermore, the digitizer could be a means by which the results of the electrophoresis test that are already in electronic form are sent digitally from an electrophoresis test apparatus to the computer, such as a modem or other device.

Figure 3:
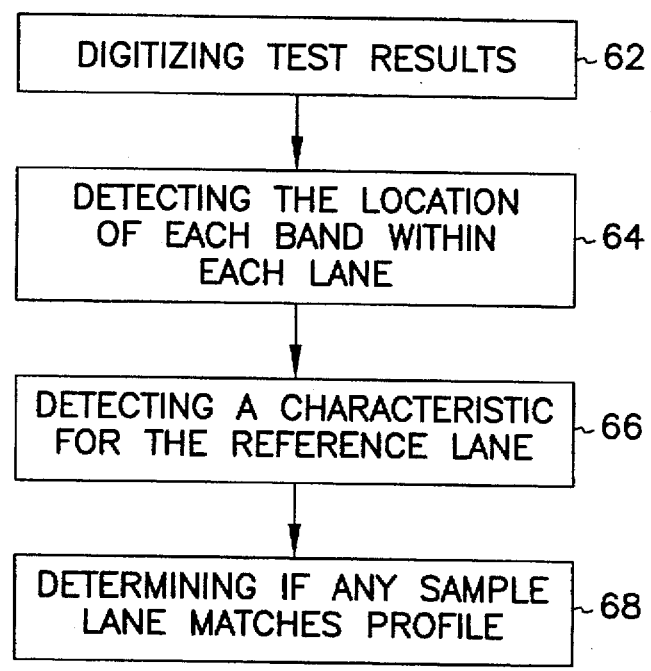
FIG. 3 is a flow chart of a method according to the present invention.

Referring now to FIG. 3, a flow chart of a method for analyzing results of an electrophoresis gel test according to the present invention is shown. In step 62, the results of the electrophoresis gel test are digitized (for example, by digitizer 62 of FIG. 2) into a format readable by a computer (for example, computer 60 of FIG. 2). This computer-readable format in one embodiment comprises a plurality of pixels organized into rows by lane, in which each pixel's density corresponds to the density of the corresponding position within the test results. Thus, a darkened series of rows of pixels within a lane corresponds to a band within that lane. In one embodiment of the invention, each pixel is capable of having a density of one of 256 shades of gray; however, the invention is not so limited. The number of pixels in each row and the number of rows of pixels are variable as well, and depends on the resolution of the digitizer. The invention itself is resolution independent, although using a digitizer having a high resolution yields more accurate analyses than one having a low resolution. The QuickTake 150 has a resolution of 640 pixel by 480 pixels.

In step 64, the location of each band within each lane are detected. In one embodiment of the invention, the location of each band within each lane is detected via an edge-detection algorithm. The location of each band is represented by Y, where Y is the number of pixels from the base line where the leading edge of the band begins. The base line is typically at Y=0. In another embodiment of the invention, Y is the number of pixels from the base line where the trailing edge of the band begins. By way of example only, as applied to the results of the electrophoresis test as shown in FIG. 1, step 64 may yield a set of data points for reference lane 12 as follows: (0, 65, 110, 140, 170, 180). Data point 0 corresponds to band 20, data point 65 corresponds to band 22, data point 110 corresponds to band 24, data point 140 corresponds to band 26, data point 170 corresponds to band 28, and data point 180 corresponds to band 30. In other words, the set of data points for reference lane 12 corresponds to the presence of a band beginning at pixel 0, viz., having a leading edge at pixel 0 (band 20), a band beginning at pixel 65 (band 22), a band beginning at pixel 110 (band 24), a band beginning at pixel 140 (band 26), a band beginning at pixel 170 (band 28) and a band beginning at pixel 180 (band 30).

In step 66, a characteristic for the particular electrophoresis test results under analysis is determined. The characteristic is a mathematical function that best predicts the location of a band corresponding to a DNA segment of a particular length. That is, the characteristic is of the form $Y=f(X)$, where X is the length of the corresponding DNA fragment and Y is the location of the band in pixels. The length of the corresponding DNA fragment for each band within a reference lane is previously known by experimentation, or alternatively can be looked up within a reference book commonly available from biological supply companies. In one embodiment of the present invention, exponential regression is applied to determine a function of best fit of the form $Y=a+(b*LN\ X)$, where a and b are coefficients determined by the exponential regression and vary per the reference lane being examined, and LN X refers to the natural logarithm of X. The characteristic is determinable because a set of points X and Y is provided by the reference lane having known length (X points) and having measured locations (Y points). Note that any characteristic accurately predicting the location of a band of a particular length can be used within the scope and spirit of the present invention. In any case, the set of all data points Y for each X is the predicted location of all the bands within the reference lane, as per the characteristic, as applied to the bands within the reference lane.

Ideally, the characteristic determined in step 66 has a correlation of 1.0. That is, that for every given DNA segment within a particular lane, the location of the corresponding band is absolutely predicted by the characteristic. The correlation therefore provides a quantitative measure of the present invention's ability to recognize properly the DNA of the reference gene of a particular electrophoresis gel test. The correlation thus is a statistical correlation comparing the actual position of a band with its position as predicted by the characteristic. With respect to the function of best fit of the form $Y=a+(b*LN\ X)$ in one embodiment of the invention, it has been found that the actual correlations are between 0.95 and 0.98. However, it has also been found that any correlation greater than 0.9 yields acceptable analysis results of electrophoresis gel tests.

In step 68, the characteristic as determined in step 66 and as applied to a profile for a genetic disorder is applied against each of the sample lanes to determine whether any of the sample lanes includes a band representing a segment for every segment with the profile. The characteristic is applied to a profile for a genetic disorder in that, for each DNA segment of the profile, the characteristic yields a corresponding data point representing the position within a lane of a band corresponding to that DNA segment. If there is a band within a sample lane for every band predicted by the characteristic as applied to the profile, that sample lane is said to match the profile. That is, if for every data point that the characteristic yielded when applied to a profile there is a corresponding data point within a sample lane, then there is a DNA segment within that sample lane corresponding to every DNA segment of the profile. If the profile is for a particular genetic disorder, then such a sample lane corresponds to a gene afflicted with that disorder.

In one embodiment of the invention, step 68 determines whether a band has been detected at every position predicted by the characteristic as applied to the profile, and whether the density of each such band is greater than a predetermined minimum darkness. That is, step 68 determines if each point of the set of data points produced by the characteristic upon application to the profile is present within the set of data points corresponding to the location of bands within a sample lane detected in step 64. If each data point is present, then step 68 further determines whether the density of the band at each position exceeds the predetermined minimum darkness, in which case the sample corresponding to the sample lane is said to match the profile.

In one embodiment of the invention, the density of each pixel ranges from 0 to 255, where 255 is black and 0 is white, and the predetermined minimum darkness is measured as a relative percentage of a density between the absolute minimum and absolute maximum density found in any lane. For example, if the predetermined minimum darkness is 50%, then as applied to electrophoresis test results in which the absolute minimum density is 100 and the absolute maximum density is 200, the predetermined minimum darkness is 100+(50%×(200−100))=150. The predetermined minimum darkness applies to the lowest density pixel for a particular row of pixels of a lane. In other words, that the density of the band at data point Y of a particular lane exceeds the predetermined minimum darkness value means that the density of each and every pixel at row Y within that lane exceeds the predetermined minimum darkness value.

Thus, for example, in the case of sample lane 16 of FIG. 1, step 64 detects the set of data points (0, 65, 110, 140, 170, 180). Also for example, assume that as applied to a predetermined profile the characteristic determined in step 66 yields the set of data points (65, 140, 170). If the density of each pixel at positions (65, 140, 170) of sample lane 16 exceeds the predetermined minimum darkness value, sample lane 16 is said to match the profile. That is, for every data point yielded by the characteristic upon application to the profile, there is a corresponding data point within sample lane 16 exceeding the predetermined minimum darkness value. If the profile is for a particular genetic disorder, then the sample gene represented by sample 16 is diagnosed as afflicted with the disorder.

Note that the presence of extraneous data points within sample lane 16 does not affect the comparison of the characteristic as applied to the predetermined profile. That is, the presence of data points (0, 110, 180) in addition to (65, 140, 170) does not affect the analysis. The presence of additional data points corresponds to an imprecise restriction on the sample gene from which sample lane 16 was taken, and does not counter the end conclusion that sample lane 16 matches the predetermined profile.

In another embodiment of the present invention, step 68 does not determine whether the density at each data point exceeds the predetermined minimum darkness value, but rather only reports the actual density at each data point (that is, the minimum density of all pixels within the row specified by that data point). In this manner, the trained technician or doctor retains a level of control over the computerized process. This is useful, for example, in the case of a "dirty" electrophoresis test where the presence of excessive noise on the digitized image compels a relatively high predetermined minimum darkness percentage to filter out noise, but which conversely also filters out legitimate data points as well.

Figure 4:
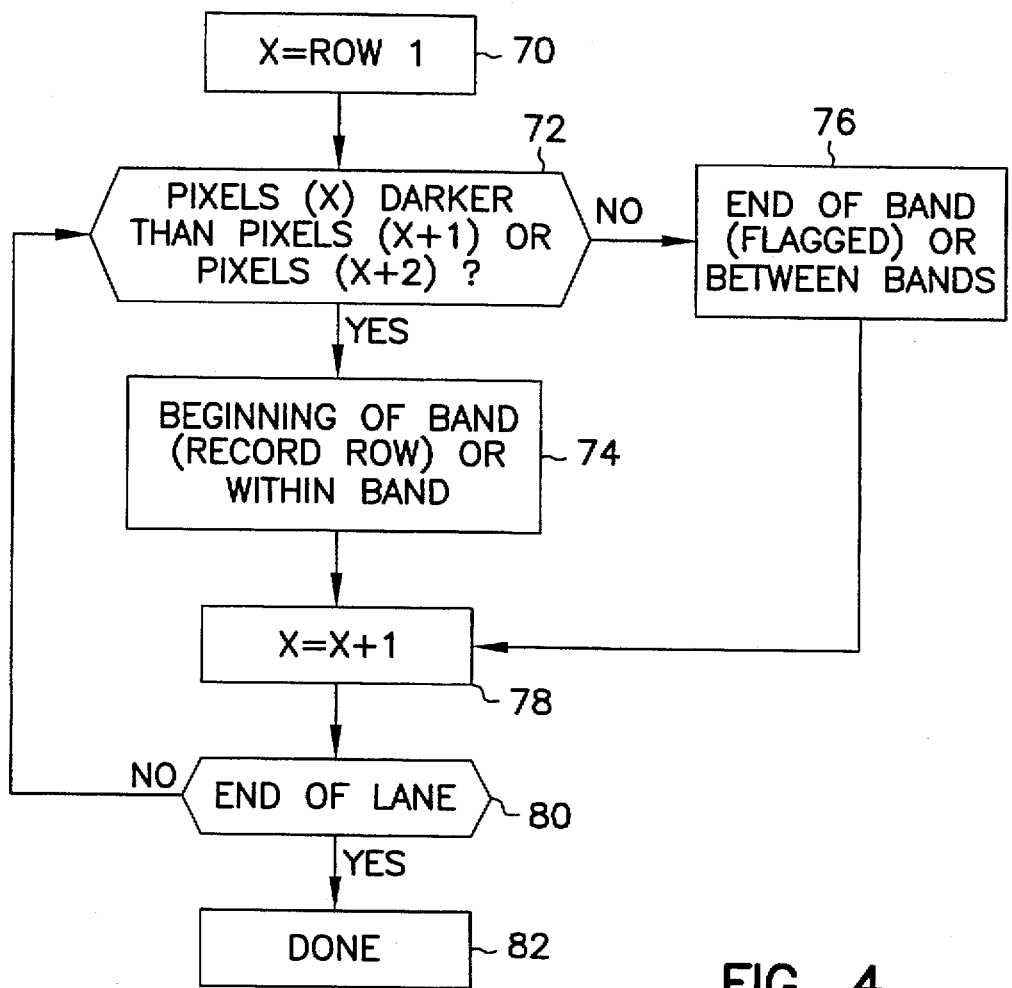
FIG. 4 is a flow chart of a method for detecting the location of each band within a particular lane of an electrophoresis test.

Referring now to FIG. 4, a flow chart of a method for detecting the location of each band within a particular lane is shown. This method is one implementation of step 64 of FIG. 3, although the present invention is not so limited. In step 70, the variable X is set to the pixel location associated with row 1, which is typically X=0. In step 72, the density of each pixel within row X is compared with the density of the corresponding pixel within both the immediately preceding row (that is, row X-1), and the row immediately preceding that row (that is, row X-2). A corresponding pixel is a pixel in a different row but in the same column. If every pixel within row X is darker (i.e., has a higher density) than either of the corresponding pixels of the preceding two rows, then control is directed to step 74, else control is directed to step 76. Note that in the case of X=0, there are no preceding rows, in which case control is automatically directed to step 76. Note also that in the case of X=1, there is only one preceding row, in which case each pixel within row X is only compared to the single preceding row.

Step 72 therefore detects the beginning of a band within a lane. If step 72 encounters a complete row of pixels that are all darker than the corresponding pixels of either of the preceding two rows of pixels, it recognizes that row as the beginning of a band in the lane. Comparing the previous two rows, as opposed to only one row, provides a measure of allowance for extraneous streaking that may occur in an electrophoresis gel test. Such extraneous streaking is typically only one pixel in width, and thus comparing the two previous rows ensures that streaking does not decrease the integrity of the present invention. As shown in FIG. 4, however, once a band has been detected, the method detects the presence of a single lower-density band as sufficient to indicate the end of a band, so that bands separated by only one row of pixels are still detected as two separate bands.

Upon direction by step 72 to step 74, step 74 records the current value of X as a data point corresponding to the location of a band if step 72 detected a row of pixels darker than either of the two preceding rows for the first time, or if the previous execution of step 72 had not detected a row of pixels darker than either of the two preceding rows. That is, step 74 records the current value of X as a data point if step 72 has detected the beginning of a new band. Otherwise, step 72 only has detected the middle or end of an already detected band. In either case, control is directed next to step 78.

Conversely, upon direction by step 72 to step 76, step 76 flags that a band has ended if step 72 had not detected a row of pixels darker than either of the two preceding rows for the first time, or if the previous execution of step 72 had detected a row of pixels darker than either of the two preceding rows. That is, step 76 flags that a band has ended if step 72 has detected the end of a band, or before the first band has been detected. Otherwise step 72 only has detected the middle of a space between bands. In either case, control is directed next to step 78.

Step 78 increase the row counter X by one. Finally, step 80 determines whether the end of the lane being analyzed has been reached. That is, step 80 determines whether X has counted past the last row within the lane. If it has not, then control is redirected to step 72, and the process starts again at that step. If the end of the lane has been reached, then step 80 directs control to step 82, and the method shown in FIG. 4 is completed. That is, the process of collecting data points corresponding to the location of the leading or trailing edge of each band within the lane being analyzed is finished.

By way of example only, and as illustrative of the method shown in FIG. 4, assume that the pixels within rows 0–8 of a lane being analyzed were as follows: light, light, dark, dark, dark, light, dark, dark, light, wherein each of the two series of dark pixels signifies a band. Thus, at step 72 when X=2 (corresponding to the first dark row of pixels), control would be directed to step 74, and the data point 2 would be recorded as the location of a band within the lane. Furthermore, at step 72 when X=5 (corresponding to the light row of pixels in between the two bands), control would be directed to step 76, and step 76 would flag that the end of a band had been detected. Finally, at step 72 when X=6 (corresponding to the beginning of the second band), control would again be directed to step 74, and the data point 6 would be recorded as the location of a second band within the lane. Therefore, when the method was finished, two data points would have been detected: 2, 6.

As has been described, the present invention provides a number of advantages. Because the invention allows for analysis of results of an electrophoresis gel test via computer, the analysis is objective and reliable, and not of suspect credibility as may result by subjective, human analysis. This is particularly significant because of the logarithmic nature of the results of electrophoresis tests. Proper visual analysis of electrophoresis test results requires a person to examine the results in a logarithmic, not linear, manner, which has proven very difficult to do. The present invention, however, eliminates the need for visual analysis.

Furthermore, because analysis is accomplished by computer, the present invention does not require significant attention from a trained doctor or technician. In addition, the computer employed to conduct the analysis according to the invention is a typical desktop PC-compatible or Macintosh computer. In this manner, the present invention provides the advantage of added minimal cost to the electrophoresis testing process; such desktop computers are typically of lower cost than the remainder of the electrophoresis testing equipment by several orders of magnitude. Moreover, the edge detection algorithm disclosed herein is only sensitive to horizontal lines, and therefore is efficient and processes test results quickly, and thus can analyze a multitude of such results in a minimum of time.

Those of ordinary skill in the art will readily appreciate that many other changes and modifications to the above drawings and description can be made without departure from the spirit or scope of the claims. For example, the invention is adaptable in that if the doctor or technician feels that a band of a sample lane that was a positive result has been ignored, the doctor can decrease the predetermined minimum darkness percentage, and then have the invention recompare the sample lane with the reference lane. For further example, scanned and analyzed test results can be stored or archived on the storage device attached to the computer, to allow for easier later retrieval as compared retrieval of stored to hard copies of the analysis results, without departure from the scope and spirit of the following claims.

I claim:

1. A computerized method for analyzing results of an electrophoresis gel test having a plurality of lanes, including a reference lane and at least one sample lane, each lane having one or more bands located throughout the lane, the method comprising the steps of:

digitizing the results of the electrophoresis gel test into a corresponding computer-readable format;

detecting the location of each band within each lane based on the computer-readable format of the results;

determining a characteristic having a best fit function based specifically on the location of each band within the reference lane, and the length of a segment corresponding to the band; and, comparing the location of each band within each sample lane with the characteristic having the best fit function as applied to a predetermined profile to determine if any sample lane matches the profile within a correlation of greater than a predetermined minimum.

2. The computerized method of claim 1, wherein the method further comprises the step of comparing the location of each band within the reference lane with the characteristic to correlate the reference lane with the characteristic.

3. The computerized method of claim 1, wherein the computer-readable format of the results comprises a plurality of pixels for each lane organized into rows.

4. The computerized method of claim 1, wherein each band within each lane has an edge, and the step of detecting the location of each band within each lane detects the edge of each band within each lane.

5. The computerized method of claim 1, wherein the step of determining a characteristic applies an exponential regression on the location each band within the reference lane and the length of the segment corresponding to the band.

6. The computerized method of claim 1, wherein the step of comparing the location of each band within each sample lane with the characteristic determines whether each sample lane includes every band as predicted by the characteristic as applied to the profile.

7. A computerized system for analyzing results of an electrophoresis gel test having a plurality of lanes, including a reference lane and at least one sample lane, each lane having one or more bands located throughout the lane, the system comprising:

a digitizer for digitizing the results of the electrophoresis gel test into a corresponding computer-readable format; and, a computer, operatively coupled to the digitizer, comprising:

means for detecting the location of each band within each lane of the computer-readable format of the results;

means for determining a characteristic having a best fit function based specifically on the location of each band within the reference lane and the length of a segment corresponding to the band; and, means for comparing the location of each band within each sample lane with the characteristic having the best fit function as applied to a predetermined profile to determine if any sample lane matches the profile within a correlation of greater than a predetermined minimum.

8. The computerized system of claim 7, wherein the computer further comprises:

a random-access memory (RAM);

a central processing unit (CPU); and, a storage device, wherein each means is stored on the storage device, and copied into the RAM and executed therefrom by the CPU.

9. The computerized system of claim 7, wherein the computer further comprises means for comparing the location of each band within the reference lane with the characteristic to correlate the reference lane with the characteristic.

10. The computerized system of claim 7, wherein the computer-readable format of the results comprises a plurality of pixels for each lane organized into rows.

11. The computerized system of claim 7, wherein each band within each lane has an edge, and the means for detecting the location of each band within each lane detects the edge of each band within each lane.

12. The computerized system of claim 7, wherein the means for determining a characteristic applies an exponential regression on the location of each band within the reference lane and the length of the segment corresponding to the band.

13. The computerized system of claim 7, wherein the means for comparing the location of each band within each sample lane with the characteristic determines whether each sample lane includes every band as predicted by the characteristic as applied to the profile.

14. A computer-readable storage medium having a computer program executable on a suitably configured computer, the computer program directing the computer to perform a method comprising the steps of:

detecting the location of each band within each lane, from results from an electrophoresis gel test, of a digitized computer-readable format;

determining a characteristic having a best fit function based specifically on the location of each band within the reference lane and the length of a DNA segment corresponding to the band; and, comparing the location of each band within each sample lane with the characteristic having the best fit function as applied to a predetermined profile to determine if any sample lane matches the profile within a correlation of greater than a predetermined minimum.

15. The storage medium of claim 14, wherein the storage medium is a floppy disk for insertion into a floppy disk drive of the suitably configured computer.

16. The storage medium of claim 14, wherein the method further comprises the step of comparing the location of each band within the reference lane with the characteristic to correlate the reference lane with the characteristic.

17. The storage medium of claim 14, wherein the computer-readable format of the results comprises a plurality of pixels for each lane organized into rows.

18. The storage medium of claim 14, wherein each band within each lane has an edge, and the means for detecting the location of each band within each lane detects the edge of each band within each lane.

19. The storage medium of claim 14, wherein the step of determining the characteristic applies an exponential regression on the location of each band within the reference lane and the length of the segment corresponding to the band.

20. The storage medium of claim 14, wherein the step of comparing the location of each band within each sample lane with the characteristic determines whether each sample lane includes every band as predicted by the characteristic as applied to the profile.

21. A computerized method for analyzing results of an electrophoresis gel test having at least one sample lane, each sample lane having one or more bands located throughout the sample lane, the method comprising the steps of:

digitizing the results of the electrophoresis gel test into a corresponding computer-readable format;

detecting the location of each band within each sample lane based on the computer-readable format of the results; and, comparing the location of each band within each sample lane with a predetermined reference characteristic having a best fit function as applied to a predetermined profile to determine if any sample lane matches the profile within a correlation of greater than a predetermined minimum, wherein the predetermined reference characteristic having the best fit function is specifically based on the location of each of a plurality of bands within a reference lane and the length of a segment corresponding to each of the plurality of bands within the reference lane.

* * * * *